(12) United States Patent
Young et al.

(10) Patent No.: US 7,256,271 B2
(45) Date of Patent: Aug. 14, 2007

(54) CANCEROUS DISEASE MODIFYING ANTIBODIES

(75) Inventors: David S. F. Young, Toronto (CA); Susan E. Hahn, Toronto (CA)

(73) Assignee: Arius Research Inc., Ontario (CA)

( * ) Notice: Subject to any disclaimer, the term of this patent is extended or adjusted under 35 U.S.C. 154(b) by 660 days.

(21) Appl. No.: 10/348,284

(22) Filed: Jan. 21, 2003

(65) Prior Publication Data

US 2004/0141915 A1    Jul. 22, 2004

(51) Int. Cl.
*C07K 16/00* (2006.01)
*C12P 21/08* (2006.01)
*A61K 39/395* (2006.01)
*A61K 39/00* (2006.01)

(52) U.S. Cl. .............. 530/387.1; 530/388.1; 530/388.8

(58) Field of Classification Search ............. 530/387.1, 530/388.1; 435/7.23
See application file for complete search history.

(56) References Cited

U.S. PATENT DOCUMENTS

| | | | |
|---|---|---|---|
| 4,861,581 | A | 8/1989 | Epstein et al. |
| 5,171,665 | A | 12/1992 | Hellstrom et al. |
| 5,484,596 | A | 1/1996 | Hanna, Jr. et al. |
| 5,693,763 | A | 12/1997 | Codington et al. |
| 5,750,102 | A | 5/1998 | Eisenbach et al. |
| 5,780,033 | A | 7/1998 | Torchilin et al. |
| 5,783,186 | A | 7/1998 | Arakawa et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |

2001/0009665 A1    7/2001    Young et al.

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-17802).*
Embleton et al (Immunol Ser, 1984, 23:181-207).*
Hsu (in Tissue Culture Methods and Applications, Kruse and Patterson, Eds, 1973, Academic Press, NY, see abstract, p. 764).*
Hill (The Basic Science of Oncology, Tannock, I. F. and Hill, H. P., eds. 1992, Ch 11, p. 178-195).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Gura (Science, 1997, 278:1041-1042).*
Jain (Sci. Am., 1994, 271:58-65).*
Curti (Crit. Rev. in Oncology/ Hematology, 1993, 14:29-39).*
Hartwell et al (Science, 1997, 278:1064-1068).*
Winter et al (TIPS, 1993, 14:139-143).*
Baselga et al (J. Clin. Oncol, 1996, 14:737-744).*
X. Duan et al, "The development and characterization of anti-cancer therapeutic monoclonal antibodies", International Journal of Cancer Supplement, No. 13, p. 444, XP008019619 (Jun. 30, 2002).

* cited by examiner

*Primary Examiner*—Susan Ungar
*Assistant Examiner*—Peter J. Reddig
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

3 Claims, 1 Drawing Sheet

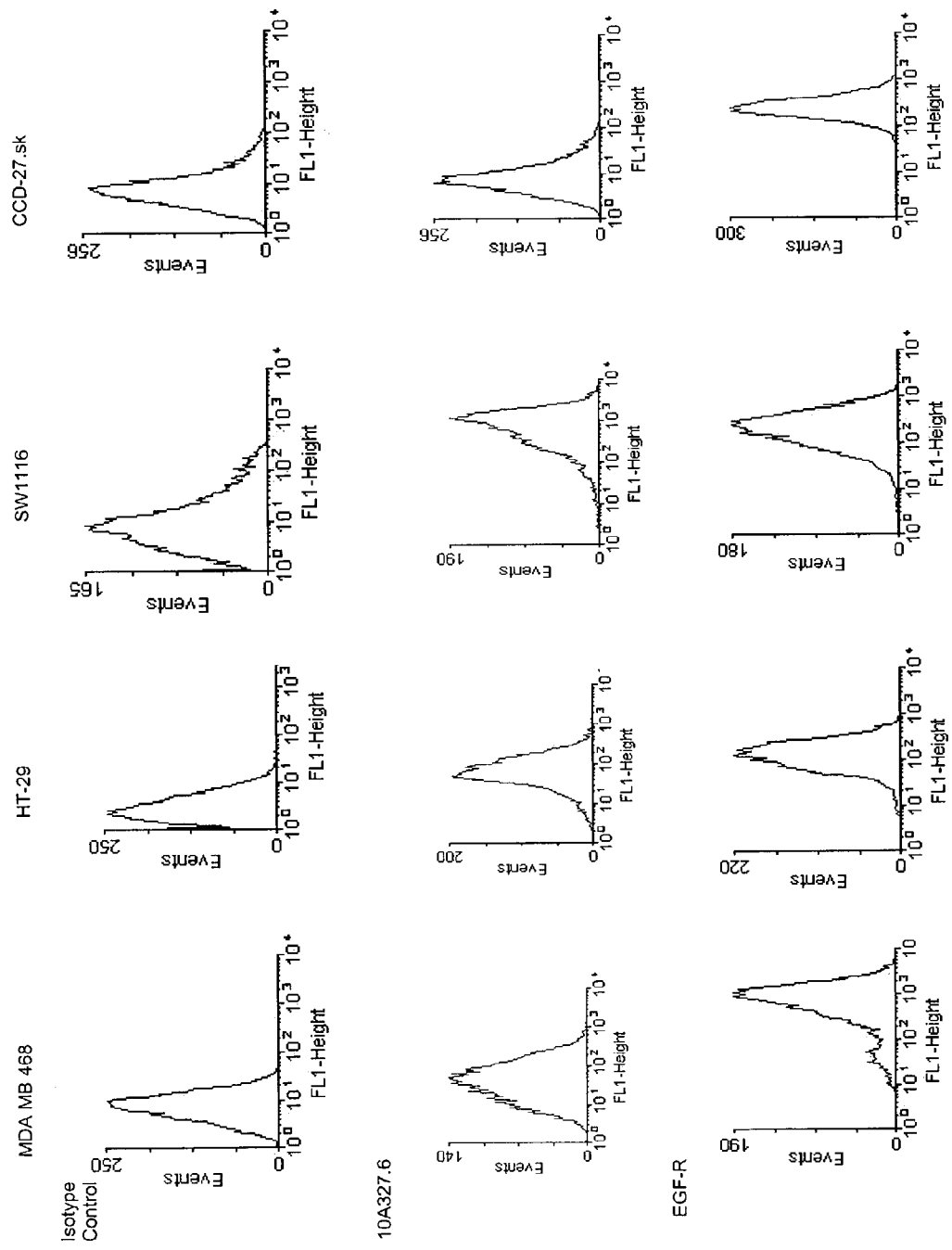

CANCEROUS DISEASE MODIFYING ANTIBODIES

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMABs of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment can not be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells.

Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-her 2 antibody in combination with Cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only one patient having a partial response. In other trials, use of 17-1A produced only one complete response and two minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibody for melanoma. Thus, it can be seen that despite successful small animal studies that are a prerequisite for human clinical trials, the antibodies that have been tested have been for the most part ineffective.

Prior Patents:

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

Furthermore, it is within the purview of this invention to conjugate standard chemotherapeutic modalities, e.g. radionuclides, with the CDMABs of the instant invention, thereby focusing the use of said chemotherapeutics.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

BRIEF DESCRIPTION OF THE FIGURES

FIG. 1 includes representative FACS histograms of 10A327.6 antibodies, isotype control antibodies, anti-EGFR antibodies directed against several cancer cell lines and non-cancer cells.

DETAILED DESCRIPTION OF THE INVENTION

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification.

One of the potential benefits of monoclonal antibodies with respect to the treatment of cancer is their ability to specifically recognize single antigens. It was thought that in some instances cancer cells possess antigens that were specific to that kind of transformed cell. It is now more frequently believed that cancer cells have few unique antigens, rather, they tend to over-express a normal antigen or express fetal antigens. Nevertheless, the use of monoclonal antibodies provided a method of delivering reproducible doses of antibodies to the patient with the expectation of better response rates than with polyclonal antibodies.

Traditionally, monoclonal antibodies have been made according to fundamental principles laid down by Kohler and Milstein. Mice are immunized with antigens, with or without adjuvants. The splenocytes are harvested from the spleen for fusion with immortalized hybridoma partners. These are seeded into microtitre plates where they can secrete antibodies into the supernatant that is used for cell culture. To select from the hybridomas that have been plated for the ones that produce antibodies of interest the hybridoma supernatants are usually tested for antibody binding to antigens in an ELISA (enzyme linked immunosorbent assay) assay. The idea is that the wells that contain the hybridoma of interest will contain antibodies that will bind most avidly to the test antigen, usually the immunizing antigen. These wells are then subcloned in limiting dilution fashion to produce monoclonal hybridomas. The selection for the clones of interest is repeated using an ELISA assay to test for antibody binding. Therefore, the principle that has been propagated is that in the production of monoclonal antibodies the hybridomas that produce the most avidly binding antibodies are the ones that are selected from among all the hybridomas that were initially produced. That is to say, the preferred antibody is the one with highest affinity for the antigen of interest.

There have been many modifications of this procedure such as using whole cells for immunization. In this method, instead of using purified antigens, entire cells are used for immunization. Another modification is the use of cellular ELISA for screening. In this method instead of using purified antigens as the target in the ELISA, fixed cells are used. In addition to ELISA tests, complement mediated cytotoxicity assays have also been used in the screening process. However, antibody-binding assays were used in conjunction with cytotoxicity tests. Thus, despite many modifications, the process of producing monoclonal antibodies relies on antibody binding to the test antigen as an endpoint.

Most antibodies directed against cancer cells have been produced using the traditional methods outlined above. These antibodies have been used both therapeutically and diagnostically. In general, for both these applications, the antibody has been used as the targeting agent that delivers a payload to the site of the cancer. These antibody conjugates can either be radioactive, toxic, or serve as an intermediary for further delivery of a drug to the body, such as an enzyme or biotin. Furthermore, it was widely held, until recently, that naked antibodies had little effect in vivo. Both HERCEPTIN and RITUXIMAB are humanized murine monoclonal antibodies that have recently been approved for human use by the FDA. However, both these antibodies were initially made by assaying for antibody binding and their direct cytotoxicity was not the primary goal during the production of hybridomas. Any tendency for these antibodies to produce tumor cell killing is thus through chance, not by design.

Although the production of monoclonal antibodies have been carried out using whole cell immunization for various applications, the screening of these hybridomas have relied on either putative or identified target antigens or on the selectivity of these hybridomas for specific tissues. It is axiomatic that the best antibodies are the ones with the highest binding constants. This concept originated from the basic biochemical principle that enzymes with the highest binding constants were the ones that were the most effective for catalyzing a reaction. This concept is applicable to receptor ligand binding where the drug molecule binding to the receptor with the greatest affinity usually has the highest probability for initiating or inhibiting a signal. However, this may not always be the case since it is possible that in certain situations there may be cases where the initiation or inhibition of a signal may be mediated through non-receptor binding. The information conveyed by a conformational change induced by ligand binding can have many consequences such as a signal transduction and endocytosis, among others. The ability to produce a conformational change in a receptor molecule may not necessarily be due to the filling of a ligand receptor pocket but may occur through the binding of another extracellular domain or due to receptor clustering induced by a multivalent ligand.

The production of antibodies to produce cell killing need not be predicated upon screening of the hybridomas for the best binding antibodies. Rather, although not advocated by those who produce monoclonal antibodies, the screening of the hybridoma supernatants for cell killing or alternatively for cessation of growth of the cancerous cells may be selected as a desirable endpoint for the production of cytotoxic or cytostatic antibodies. It is well understood that in-vivo antibodies mediate their function through the Fc portions and that part of the utility of the therapeutic antibody is determined by the functionality of the constant region or attached moieties. In this case the FAb portion of the antibody, the antigen-combining portion, commonly referred to as the antigen binding fragment, will confer to the antibody its specificity and the Fc portion its functionality. The antigen combining site of the antibody can be considered to be the product of a natural combinatorial library. The result of the rearrangement of the variable region of the antibody can be considered a molecular combinatorial library where the output is a peptide. Therefore, the sampling of this combinatorial library can be based on any parameter. Like sampling a natural compound library for antibiotics, it is possible to sample an antibody library for cytotoxic or cytostatic compounds.

The various endpoints in a screen must be differentiated from each other. For example, the difference between antibody binding to the cell is distinct from cell killing. Cell killing (cytotoxicity) is distinct from the mechanisms of cell death such as oncosis or apoptosis. There can be many processes by which cell death is achieved and some of these can lead either to oncosis or apoptosis. There is speculation that there are other cell death mechanisms other than oncosis or apoptosis but regardless of how the cell arrives at death there are some commonalities of cell death. One of these is the absence of metabolism and another is the denaturation of enzymes. In either case vital stains will fail to stain these cells. These endpoints of cell death have been long understood and predate the current understanding of the mechanisms of cell death. Furthermore, there is the distinction between cytotoxic effects where cells are killed and cytostatic effects where the proliferation of cells are inhibited.

In a preferred embodiment of the present invention, the assay is conducted by focusing on cytotoxic activity toward cancerous cells as an end point. In a preferred embodiment, a live/dead assay kit, for example the LIVE/DEAD® Viability/Cytotoxicity Assay Kit (L-3224) by Molecular Probes, is utilized. The Molecular Probes kit provides a two-color fluorescence cell viability assay that is based on the simultaneous determination of live and dead cells with two probes that measure two recognized parameters of cell viability—intracellular esterase activity and plasma membrane integrity. The assay principles are general and applicable to most eukaryotic cell types, including adherent cells and certain tissues, but not to bacteria or yeast. This fluorescence-based method of assessing cell viability is preferred in place of such assays as trypan blue exclusion, Cr release and similar methods for determining cell viability and cytotoxicity.

In carrying out the assay, live cells are distinguished by the presence of ubiquitous intracellular esterase activity, determined by the enzymatic conversion of the virtually nonfluorescent cell-permeant CALCEIN AM to the intensely fluorescent Calcein. The polyanionic dye Calcein is well retained within live cells, producing an intense uniform green fluorescence in live cells (ex/em~495 nm/~515 nm). EthD-1 enters cells with damaged membranes and undergoes a 40-fold enhancement of fluorescence upon binding to nucleic acids, thereby producing a bright red fluorescence in dead cells (ex/em~495 nm/~635 nm). EthD-1 is excluded by the intact plasma membrane of live cells. The determination of cell viability depends on these physical and biochemical properties of cells. Cytotoxic events that do not affect these cell properties may not be accurately assessed using this method. Background fluorescence levels are inherently low with this assay technique because the dyes are virtually nonfluorescent before interacting with cells.

In addition to the various endpoints for screening, there are two other major characteristics of the screening process. The library of antibody gene products is not a random library but is the product of a biasing procedure. In the examples below, the biasing is produced by immunizing mice with cells. This increases the proportion of antibodies that have the potential to bind the target antigen. Although immunization is thought of as a way to produce higher affinity antibodies (affinity maturation) in this case it is not. Rather, it can be considered as a way to shift the set of antigen combining sites towards the targets. This is also distinct from the concept of isotype switching where the functionality, as dictated by the constant portion of the heavy chain, is altered from the initial IgM isotype to another isotype such as IgG.

The third key feature that is crucial in the screening process is the use of multitarget screening. To a certain extent specificity is related to affinity. An example of this is the situation where an antigen has very limited tissue distribution and the affinity of the antibody is a key determinant of the specificity of the antibody-the higher the affinity the more tissue specific the antibody and likewise an antibody with low affinity may bind to tissues other than the one of interest. Therefore, to address the specificity issue the antibodies are screened simultaneously against a variety of cells. In the examples below the hybridoma supernatants (representing the earliest stages of monoclonal antibody development), are tested against a number of cell lines to establish specificity as well as activity.

The antibodies are designed for therapeutic treatment of cancer in patients. Ideally the antibodies can be naked antibodies. They can also be conjugated to a cytotoxic moiety, such as any of the well-known chemotherapeutic agents, or alternatively radioactive isotopes or toxins. They can be used to target other molecules to the cancer. e.g. biotin conjugated enzymes. When radioactive compounds are used for conjugation, enhanced imaging capability is achieved as well.

The antibodies can be fragmented and rearranged molecularly. For example Fv fragments can be made; sFv-single chain Fv fragments; diabodies etc.

It is envisioned that these cancerous disease modifying antibodies or antigen binding fragments thereof can be used for diagnosis, prognosis, and monitoring of cancer. For example the patients can have blood samples drawn for shed tumor antigens which can be detected by these antibodies in different formats such as ELISA assays, rapid test panel formats etc. The antibodies can be used to stain tumor biopsies for the purposes of diagnosis. In addition a panel of therapeutic antibodies can be used to test patient samples to determine if there are any suitable antibodies for therapeutic use.

EXAMPLE 1

Hybridomas Production—Hybridoma Cell Line 10A327.6

The hybridoma cell line 10A327.6 was deposited, in accordance with the Budapest Treaty, with the American Type Culture Collection, 10801 University Blvd., Manassas, Va. 20110 -2209 on Nov. 26, 2002, under Accession Number PTA-4829. In accordance with 37 CFR 1.808, the depositors assure that all restrictions imposed on the availability to the public of the deposited materials will be irrevocably removed upon the granting of a patent. The deposit will be replaced if viable samples cannot be dispensed by the depository.

To produce the hybridoma that produces anti-cancer antibody single cell suspensions of human colon cancer cells were prepared in cold PBS. IMMUNEASY™ (Qiagen, Venlo, Netherlands) adjuvant was prepared for use by gentle vortexing. 100 microliters of IMMUNEASY™ mouse adjuvant were added to 10 million colon cancer cells in the microcentrifuge tube and mixed and left at room temperature for 15 min. Eight to nine week old BALB/c mice were immunized by injecting 100 microliters of the antigen-adjuvant containing 2.5 million cells intramuscularly. Freshly prepared antigen-adjuvant was used to boost the immunized mice two weeks after the initial immunization at 2.5 million cells in 250 microliters by an intraperitoneal injection. A spleen was used for fusion two days after the last immunization. The hybnidomas were prepared by fusing the isolated splenocytes with NSO-1 myeloma partners. The supernatants from the fusions were tested for subcloning of the hybridomas.

To determine whether the antibodies secreted by hybridoma cells are of the IgG or IgM isotype, an ELISA assay was employed. 100 microliters/well of goat anti-mouse IgG+IgM (H+L) at a concentration of 2.4 micrograms/mL in coating buffer (0.1M carbonate/bicarbonate buffer, pH 9.2-9.6) at 4° C. was added to the ELISA plates overnight. The plates were washed thrice in washing buffer (PBS+0.05% Tween). 100 microliters/well blocking buffer (5% milk in wash buffer) was added to the plate for 1 hr. at room temperature and then washed thrice in washing buffer. 100 microliters/well of hybridoma supernatant was added and the plate incubated for 1 hr. at room temperature. The plates were washed thrice with washing buffer and 1/5000 dilution of either goat anti-mouse IgG or IgM horseradish peroxidase conjugate (diluted in PBS containing 1% bovine serum albumin), 100 microliters/well, was added. After incubating the plate for 1 hr. at room temperature the plate was washed thrice with washing buffer. 100 microliters/well of TMB solution was incubated for 1-3 minutes at room temperature. The color reaction was terminated by adding 100 microliters/well 2M $H_2SO_4$ and the plate was read at 450 nm with a Perkin-Elmer HTS7000 plate reader. As indicated in Table 1 the 10A327.6 hybridomas secreted primarily antibodies of the IgG isotype After one round of limiting dilution, hybridoma supernatants were tested for antibodies that bound to target cells in a cell ELISA assay. Three colon cancer cell lines were tested: HT-29, SW1116 and SW620. The plated cells were fixed prior to use. The plates were washed thrice with PBS containing $MgCl_2$ and $CaCl_2$ at room temperature. 100 microliters of 2% paraformaldehyde diluted in PBS was added to each well for ten minutes at room temperature and then discarded. The plates were again washed with PBS containing $MgCl_2$ and $CaCl_2$ three times at room temperature. Blocking was done with 100 microliters/well of 5% milk in wash buffer (PBS+0.05% Tween) for 1 hr at room temperature. The plates were washed thrice with wash buffer and the hybridoma supernatant was added at 100 microliters/well for 1 hr at room temperature. The plates were washed three times with wash buffer and 100 microliters/well of 1/5000 dilution of goat anti-mouse IgG or IgM antibody conjugated to horseradish peroxidase (diluted in PBS containing 1% bovine serum albumin) was added. After a one hour incubation at room temperature the plates were washed three times with wash buffer and 100 microliter/well of TMB substrate was incubated for 1-3 minutes at room temperature. The reaction was terminated with 100 microliters/well 2M $H_2SO_4$ and the plate read at 450 nm with a Perkin-Elmer HTS7000 plate reader. The results as tabulated in Table 1 were expressed as the number of folds above background compared to the IgG isotype control (3BD-27). The antibodies from the 10A327.6 hybridoma had 7.2 fold greater binding above control in the HT-29 cell line, and 23.7 fold greater binding in the SW1116 cell line. This indicated that the antibody bound differentially to an antigen that was expressed more so on some cancer cells than others.

In conjunction with testing for antibody binding the cytotoxic effect of the hybridoma supernatants were tested in the same colon cancer cell lines: HT-29, SW1116 and SW620. The Live/Dead cytotoxicity assay was obtained from Molecular Probes (Eu, Oreg.). The assays were performed according to the manufacturer's instructions with the changes outlined below. Cells were plated before the assay at the predetermined appropriate density. After 2 days, 100 microliters of supernatant from the hybridoma microtitre plates were transferred to the cell plates and incubated in a 5% $CO_2$ incubator for 5 days. The wells that served as the positive controls were aspirated until empty and 100 microliters of sodium azide and/or cycloheximide was added. 3BD-27 monoclonal antibody was also added as an isotype control since it was known not to bind to HT-29 colon cancer cells. An anti-EGFR antibody (C225) was also used in the assay for comparison. After 5 days of treatment, the plate was then emptied by inverting and blotted dry. Room temperature DPBS containing $MgCl_2$ and $CaCl_2$ was dispensed into each well from a multichannel squeeze bottle, tapped three times, emptied by inversion, and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results were tabulated in Table 1. The 10A327.6 hybridoma antibodies in the supernatant produced 16% cytotoxicity in HT-29 cells and 28% cytotoxicity in SW1116 cells. This indicated the antibody derived from the hybridoma cell can produce cytotoxicity in cancer cells. As shown in Table 1 there was a tendency to produce cytotoxicity when the antibody bound the cell being tested. This was seen in the example of 16% HT-29 cytotoxicity associated with a 7.2 fold increase in binding over the background. In another example there was a 28% cytotoxicity in SW1116 colon cancer associated with a 23.7 fold increase in binding over the background. In this example when there was no significant binding of the antibody to SW620 colon cancer cells there was no significant cytotoxicity. As tabulated in Table 1 the 3BD-27 antibody, of the same isotype as the 10A327.6 antibody and previously known not to bind to HT-29 colon cancer cells, did not produce cytotoxicity in that cancer cell line. The known non-specific cytotoxic agents sodium azide and cycloheximide produced cytotoxicity as expected. By way of comparison the well defined anti-cancer antibody C225 produced 13% cytotoxicity in SW1116 cancer cells. As shown in Table I the antibodies from the hybridoma 10A327.6 produced cytotoxicity against cancers from different individuals, bound to those cancer cells, and had properties of specificity in that the antibodies produced no cytotoxicity when that antibody did not bind to those cells.

specificity unknown, IgG2b, kappa, 20 mg/mL), J606 (anti-fructosan, IgG3, kappa, 20 mg/mL), IgG Buffer (2%)) controls in a cytotoxicity assay (Table 2).

Breast cancer (MB-231, MB-468, MCF-7), colon cancer (HT-29, SW1116, SW620), lung cancer (NCI H460), ovarian cancer (OVCAR), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody was diluted into media, and then were transferred to the cell plates and incubated in a 5% $CO_2$ incubator for 5 days. The

TABLE 1

| Clone | Isotype ELISA Fold (above bkgd) | | Cytotoxicity (%) | | | | | | Binding (above bkgd) | | |
|---|---|---|---|---|---|---|---|---|---|---|---|
| | | | HT-29 | | SW1116 | | SW620 | | HT-29 | SW1116 | SW620 |
| | IgG | IgM | Average | CV | Average | CV | Average | CV | Fold | Fold | Fold |
| 10A327.6 | 23.4 | 1.4 | 16 | 15 | 28 | 0 | 2 | 12 | 7.2 | 23.7 | 1.0 |
| 3BD-27 | | | −34 | 5 | −26 | 12 | 76 | 49 | | | |
| NaN$_3$ | | | 61 | 10 | | | 68 | 16 | | | |
| Cycloheximide | | | 23 | 8 | 17 | 14 | −2 | 8 | | | |
| anti-EGFR (C225) | | | | | 13 | 10 | | | | | |

EXAMPLE 2

Antibody Production

10A327.6 monoclonal antibody was produced by culturing the hybridomas in CL-1000 flasks (BD Biosciences, Oakville, ON) with collections and reseeding occurring twice/week and standard antibody purification procedures with Protein G Sepharose 4 Fast Flow (Amersham Biosciences, Baie d'Urfé, QC). It is within the scope of this invention to utilize monoclonal antibodies which are humanized, chimerized or murine antibodies. 10A327.6 was compared to a number of both positive (anti-Fas (EOS9.1, IgM, kappa, 20 mg/mL, eBioscience, San Diego, Calif.), anti-Her2/neu (IgG1, kappa, 10 mg/mL, Inter Medico, Markham, ON), anti-EGFR (C225, IgGI, kappa, 5 mg/mL, Cedarlane, Hornby, ON), Cycloheximide (100 mM, Sigma, Oakville, ON), NaN$_3$ (0.1%, Sigma, Oakville, ON)) and negative (107.3 (anti-TNP, IgG1, kappa, 20 mg/mL, BD Biosciences, Oakville, ON), G155-178 (anti-TNP, IgG2a, kappa, 20 mg/mL, BD Biosciences, Oakville, ON), MPC-11 (antigenic plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel and the results were tabulated in Table 2.

The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 2 represented inconsistent or effects less than the threshold cytotoxicity. The 10A327.6 produced 90% cytotoxicity in an ovarian cancer cell line compared to C225, a well studied anti-cancer antibody, demonstrating properties of specific cytotoxicity towards cancer cells.

TABLE 2

| | | BREAST | | | COLON | | | LUNG | OVARY | PROSTATE | NORMAL | |
|---|---|---|---|---|---|---|---|---|---|---|---|---|
| | | | | | | | | | | | CCD | |
| | | MB-231 | MB-468 | MCF-7 | HT-29 | SW1116 | SW620 | NCI H460 | OVCAR | PC-3 | 27sk | Hs888Lu |
| | 10A327.6 (20 μg/mL) | | | | | | | | + | | | |
| Positive Controls | anti-Fas (20 μg/mL) | | +++ | | | | | | +++ | + | − | + |
| | anti-Her2/neu | + | | + | | | | | + | − | − | − |

TABLE 2-continued

|  |  | BREAST | | | COLON | | | LUNG | OVARY | PROSTATE | NORMAL | |
|---|---|---|---|---|---|---|---|---|---|---|---|---|
|  |  | | | | | | | | | | CCD | |
|  |  | MB-231 | MB-468 | MCF-7 | HT-29 | SW1116 | SW620 | NCI H460 | OVCAR | PC-3 | 27sk | Hs888Lu |
|  | (10 µg/mL) anti-EGFR (C225, 5 µg/mL) |  | +++ | + |  | +++ |  |  | + | − | + | − |
|  | Cycloheximide (100 µm) | +++ | +++ | +++ | +++ | +++ | +++ | +++ | +++ | +++ | +++ | +++ |
|  | NaN$_3$ (0.1%) | +++ | +++ | +++ | +++ |  |  | +++ | +++ | +++ |  |  |
| Negative Controls | 107.3 (IgG1, 20 µg/mL) |  |  |  |  |  |  | +++ |  | + |  |  |
|  | G155-178 (IgG2a, 20 µg/mL) |  |  | +++ |  | + |  |  |  |  |  |  |
|  | MPC-11 (IgG2b, 20 µg/mL) |  |  | +++ |  |  |  |  |  |  |  |  |
|  | J606 (IgG3, 20 µg/mL) |  |  |  |  |  |  |  |  |  |  |  |
|  | IgG Buffer (2%) | + |  |  |  |  |  |  |  |  |  |  |

Importantly the isolated antibody did not produce cytotoxicity against a number of non-cancer cells such as CCD 27sk or Hs888 Lu. The chemical cytotoxic agents induced their expected cytotoxicity while a number of other antibodies which were included for comparison also performed as expected given the limitations of biological cell assays. It was observed the MCF-7 breast cancer cell line had cytotoxicity in response to two negative control antibodies and the results from the anti-Fas, anti-Her2/neu, and anti-EGFR antibodies may be due to an increased susceptibility to antibodies in general. However, it was also observed 10A327.6 antibodies did not produce cytotoxicity in MCF-7 cancer cells, another possible indication of specificity due to combination of antibody activity and antigen expression.

Cells were prepared for FACS by initially washing the cell monolayer with DPBS (without Ca$^{++}$ and Mg$^{++}$). Cell dissociation buffer (INVITROGEN) was then used to dislodge the cells from their cell culture plates at 37° C. After centrifugation and collection the cells were resuspended in Dulbecco's phosphate buffered saline containing MgCl$_2$ and CaCl$_2$, containing 25% fetal bovine serum at 4° C. (wash media) and counted, aliquoted to appropriate cell density, spun down to pellet the cells and resuspended in staining media (DPBS containing MgCl$_2$, CaCl$_2$ and 2% fetal bovine serum) at 4° C. in the presence of test antibodies (10A327.6) or control antibodies (isotype control or anti-EGF-R) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL propidium iodide. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1-5 units. Live cells were acquired by gating for FSC and propidium iodide exclusion. For each sample, approximately 10,000 live cells were acquired for analysis and the results presented in Table 3.

Table 3 tabulated the mean fluorescence intensity fold increase above isotype control and is presented qualitatively as: less than 5 (−); 5 to 50 (+); 50 to 100 (++); above 100 (+++) and in parenthesis, the percentage of cells stained.

TABLE 3

| ANTIBODY | Isotype | MB-231 | MB-468 | MCF-7 | HT-29 | SW1116 | SW620 | NCI-H460 | OVCAR-3 | PC-3 | CCD-27sk | Hs888 Lu |
|---|---|---|---|---|---|---|---|---|---|---|---|---|
| 10A327.6 | IgG2b, k | − | +(54%) | − | +(85%) | ++ | − | − | − | − | − | − |
| anti-EGFR | IgG1, k | ++ | ++bimodal | − | +(97%) | +(43%) | − | +Bimodal (80%) | +(90%) | +(95%) | +(50%) | +(95%) |
| anti-Fas | IgM, k | − | − | − | +(30%) | − | − | +(61%) | − | − | +(48%) | +(71%) |

Representative histograms of 10A327.6 antibodies were compiled for FIG. 1 and evidence the binding characteristics of the 10A327.6 antibody, inclusive, in some instances, of bimodal peaks.

10A327.6 displayed binding to both breast cancers (MDA-MB-231) and colon cancers (HT-29, SW1116) and no binding to the normal skin line, CCD-27sk, an indication of the specificity of the antibody. The shift in fluorescence intensity between the two types of colon cancer cells is an indication that 10A327.6 antibody binds differentially to the colon cancer cells.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated monoclonal antibody or antigen binding fragments thereof encoded by the clone deposited with the ATCC as Accession Number PTA-4829.

2. The isolated antibody or antigen binding fragments of claim 1, wherein said isolated antibody or antigen binding fragments thereof is a murine antibody.

3. The isolated clone deposited with the ATCC as Accession Number PTA-4829.

* * * * *